United States Patent [19]

Gravestock

[11] Patent Number: 4,849,516

[45] Date of Patent: Jul. 18, 1989

[54] OXADIAZINES

[75] Inventor: Michael B. Gravestock, Camberley, England

[73] Assignee: Imperial Chemical Industries PLC, London, England

[21] Appl. No.: 109,263

[22] Filed: Oct. 14, 1987

[30] Foreign Application Priority Data

Oct. 17, 1986 [GB] United Kingdom ............... 8624906

[51] Int. Cl.$^4$ ........................................... C07D 498/04
[52] U.S. Cl. .................................. 540/300; 540/200; 540/302; 540/310; 544/66
[58] Field of Search ......................................... 540/300

[56] References Cited

U.S. PATENT DOCUMENTS 4,245,089  1/1981  Ponsford et al. ............... 540/300

OTHER PUBLICATIONS

H. Gnichtel; Chemische Berichte, vol. 103, No. 11, 1970, pp. 3442–3447 Chemie Der Amino–Oxime, I.V. Die Umsetzung Von Syn-Alpha-Ketoximen Mit Aldehyden.

T. C. Smale; Tetrahedron Letters, vol. 25, No. 27, 1984,

A Chiral Intermediate for Thienamycin Analogue Synthesis: (3S, 4R)-4-(2-Azetidin-2-One.

Primary Examiner—Richard L. Raymond
Attorney, Agent, or Firm—Cushman, Darby & Cushman

[57] ABSTRACT

Compounds of the formula (V):

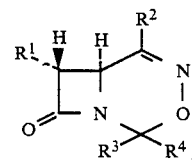

wherein $R^1$ is certain optionally substituted alkyl groups, $R^2$ is hydrogen, alkyl or optionally substituted phenyl and $R^3$ and $R^4$ are independently alkyl or optionally substituted phenyl, or together form a $C_{4-7}$ cycloalkyl ring; are described as useful intermediates in the preparation of carbapenem and penem antibiotics. Processes for their preparation are described as are certain oxadiazine intermediates.

3 Claims, No Drawings

OXADIAZINES

The present invention relates to oxadiazines which are useful intermediates in the synthesis of β-lactam antibiotics, in particular in the synthesis of carbapenems and penems.

In the past few years many groups of research workers have investigated the synthesis of carbapenems, penems, monobactams and penicillin and cephalosporin analogues. These syntheses have depended to a large extent on the ability to control stereochemistry and on the ability to prepare key intermediates conveniently and in good yields. One such class of azetidinone intermediates is that of the formula (I):

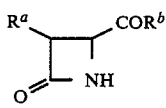
(I)

wherein $R^a$ and $R^b$ represent a variety of organic groups. The group $R^bCO$— can be converted into a variety of groups at the 4-position of the azetidinone ring; typically such groups are subsequently cyclized on to the nitrogen atom or on to a suitable substituent on said nitrogen atom to form carbapenems and penems. For example, as described in EP-A-181831, a compound of the formula (II) is subjected to a Baeyer-Villiger reaction with peracid to form a compound of the formula (III) which is subsequently converted to a penem of formula (IV) via displacement of the PhCOO— substituent, elaboration of the N-substituent, cyclization and deprotection.

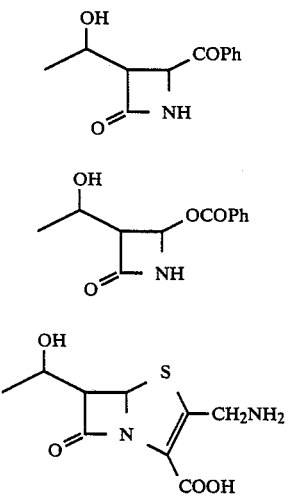

The present invention is directed towards an improved process for preparing compounds of the formula (I) and in particular to useful intermediates in the process for preparing such compounds.

Accordingly the present invention provides the compounds of the formula (V):

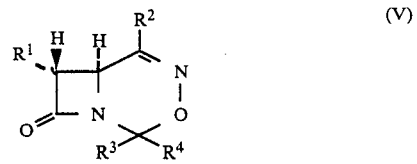
(V)

wherein: $R^1$ is $C_{1-4}$ alkyl optionally substituted by at least one optionally protected hydroxy group or fluoro; $R^2$ is hydrogen, $C_{1-4}$alkyl or optionally substituted phenyl; and $R^3$ and $R^4$ are independently $C_{1-4}$ alkyl, optionally substituted phenyl or together with the carbon atom to which they are attached from a $C_{4-7}$ cycloalkyl ring optionally substituted by $C_{1-4}$alkyl.

In particular $R^1$ is 1-fluoroethyl, 1-hydroxyethyl or 1-hydroxyprop-2-yl. Preferably $R^1$ is 1-hydroxyethyl.

In one aspect $R^2$ is optionally substituted phenyl such as phenyl substituted by $C_{1-4}$alkoxy for example methoxy, $C_{1-4}$alkyl for example methyl or halo for example chloro or bromo. In another aspect $R^2$ is $C_{1-4}$alkyl for example methyl. Preferably $R^2$ is phenyl.

In one aspect $R^3$ and $R^4$, which are preferably the same for synthetic convenience, are both optionally substituted phenyl such as phenyl substituted by $C_{1-4}$alkoxy (for example methoxy), $C_{1-4}$alkyl (for example methyl) or substituted by halo (for example chloro or bromo). Preferably $R^3$ and $R^4$ are both $C_{1-4}$alkyl for example methyl or they are joined to form, together with the carbon atom to which they are attached, a cyclohexyl ring optionally substituted by methyl.

In another aspect the present invention provides a process for preparing a compound of the formula (VI):

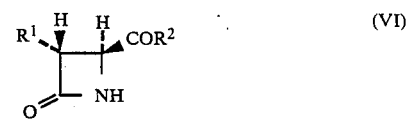
(VI)

wherein $R^1$ and $R^2$ are as hereinbefore define, which process comprises hydrolysing a compound of the formula (V).

Conveniently the hydrolysis is performed under acidic conditions for example using a dilute aqueous mineral acid such as hydrochloric acid. Typically the hydrolysis is carried out in a solvent such as acetone or a $C_{1-4}$ alkanol for example methanol or ethanol.

As stated previously the compounds of the formula (VI) are useful in preparing carbapenems and penems. Thus in a further aspect of the invention there is provided a process for preparing a compound of the formula (VII):

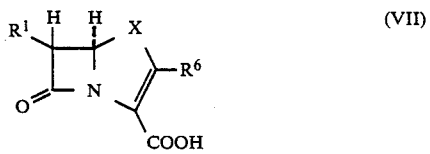
(VII)

wherein $R^1$ is as hereinabove defined, $R^6$ is a substituent known in the carbapenem and/or penem art and X is a sulphur atom or a group —$CR^7R^8$— wherein $R^7$ and $R^8$ are substituents known in the carbapenem art, which process comprises the step of hydrolysing a compound of the formula (V) to a compound of the formula (VI).

In a further aspect of the present invention there is provided a process for preparing the compounds of the formula (V) which process comprises cyclising a compound of the formula (VIII):

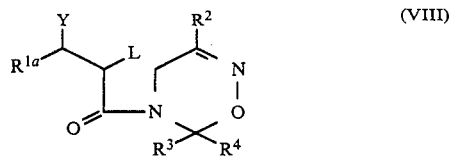

wherein $R^2$, $R^3$ and $R^4$ are as hereinbefore defined, L is a leaving group and $R^{1a}C(Y)$— represents the group $R^1$ or Y and L together with the carbon atoms to which they are attached form an epoxide group.

A particular value of L is halo, preferably bromo.

A particular value of Y is hydroxy or protected hydroxy and $R^{1a}$ is in particular methyl.

Preferred compounds of the formula (VIII) are those of the formula (IX):

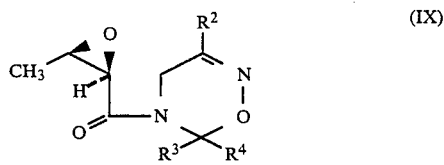

wherein $R^2$, $R^3$ and $R^4$ are as hereinafter defined.

The compounds of the formulae (VIII) and (IX) can be cyclized by treatment with a base of low nucleophilicity, for example $LiN(Si(CH_3)_3)_2$ in a solvent such as diethyl ether, t-butylmethylether or tetrahydrofuran at a non-extreme temperature for example between 0° C. and 30° C. Compounds of the formula (V) wherein $R^1$ bears a protected hydroxy group can be formed by quenching the reaction mixture in situ with a source of the protecting group for example trimethylsilyl chloride or acetyl chloride.

The compounds of the formula (VIII) are novel and form a further aspect of the present invention. The compound of the formula (IX) is a preferred feature of this aspect of the invention.

In another aspect of the present invention there is provided a process for preparing the compounds of the formula (VIII) which comprises reacting a compound of the formula (X) with a compound of the formula (XI) or a reactive derivative thereof:

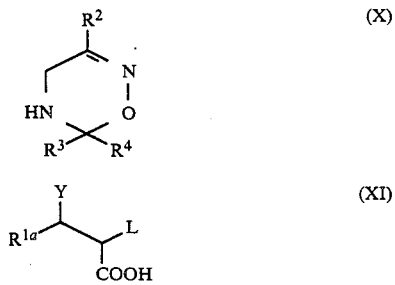

wherein $R^2$, $R^3$, $R^4$, $R^{1a}$, Y and L are as hereinbefore defined.

The reaction between the compounds of the formulae (X) and (XI) is performed under conventional acylation conditions for example in the presence of a suitable coupling agent. For example a 2,3-epoxybutanoic acid may be reacted with a compound of the formula (X), in the presence of a coupling agent, in an inert solvent for example a chlorinated hydrocarbon (e.g. dichloromethane) or an ether (e.g. tetrahydrofuran) at a suitable non-extreme temperature for example between 0° C. and 30° C.

The compounds of the formula (X) are novel and form a further aspect of the present invention.

The compounds of the formula (X) may be prepared by the reaction of a ketone of formula (XII):

with a (Z)-oxime of the formula (XIII):

wherein $R^2$, $R^3$ and $R^4$ are as hereinbefore defined, by methods analogous to those described by M. Busch et al, J. Prakt. Chem. 150, 1–39 (1937) and Chem. Ber 63, 651 (1930) and by H. Gnichtel, Chem. Ber. 103, 3442 (1970) for the reaction of aldehydes with oximes.

The oximes of the formula (XIII) may be prepared by reacting a compound of formula (XIV):

wherein $R^2$ is a hereinbefore defined, with hydroxylamine. Conveniently the compound of the formula (XIV) is in the form of an acid addition salt, eg a hydrohalide such as the hydrochloride, and conveniently hydroxylamine is in the form of an acid addition salt eg a hydrohalide such as the hydrochloride, for example as described by S. Gabriel et al, Chem. Ber. 30, 1127 (1897).

Certain compounds of the formula (XIV), for example aminoacetophenone hydrochloride, are commercially available. Otherwise they can be made by known methods for example as described by C. Mannich et al Chem. Ber. 44, 1542, (1911) or K. H. Slotta et al, Chem. Ber. 63, 1024, (1930), or by methods analogous thereto.

Preferred compounds of the formulae (VIII) and (X) are those with the groups preferred for the compounds of the formula (V).

When reference is made to protecting groups herein such protecting groups may in general be chosen from any of the groups described in the literature or known to the skilled chemist, and may be introduced by conventional methods.

Protecting groups may be removed by any convenient method as described in the literature or known to the skilled chemist, such methods being chosen so as to effect removal of the protecting group with minimum disturbance of groups elsewhere in the molecule.

Specific examples are given below for the sake of convenience, in which "lower" signifies that the group to which it is applied preferably has 1-4 carbon atoms.

It will be understood that these examples are not exhaustive. Where specific examples of methods for the removal of protecting groups are given below these are similarly not exhaustive. The use of protecting groups and methods of deprotection not specificaly mentioned is of course within the scope of the invention.

Examples of hydroxyl protecting groups include lower alkoxycarbonyl groups (eg t-butoxycarbonyl); lower alkenyloxycarbonyl groups (eg allyloxycarbonyl); halo lower alkoxycarbonyl groups (eg 2-iodoethoxycarbonyl, 2,2,2-trichloroethoxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri lower alkylsilyl (eg trimethylsilyl, t-butyldimethylsilyl), triisopropylsilyl and dimethyl-1,1,2-trimethylpropylsilyl)aryloxydialkylsilyl (eg 2,6-di-t-butyl-4-methylphenoxydimethylsilyl), diarylalkylsilyl (eg t-butyldiphenylsilyl); aryl lower alkyl (eg benzyl) and aroyl (eg 3,5-dinitrobenzoyl) groups.

Methods suitable for the removal of such hydroxyl protecting groups include hydroylsis, optionally acid or base catalysed.

The following examples are provided to illustrate the invention without implying any limitation of the scope thereof. Mplc means medium pressure liquid chromatography. Standard abbreviations (s=singlet, d=doublet, t=triplet, q=quartet, br=broad, m=multiplet) are used in the quotation of nmr (nuclear magnetic resonance) data. Mass spectral data were obtained either by Electron Impact (EI) or Chemical Ionization (CI) methods.

EXAMPLE 1

4S-Benzyl-3S-(1R-hydroxyethyl)-trans-azetidin-2-one (1'R,6S,7S)-2,2-Dimethyl-7-(1-hydroxyethyl)-8-oxo-5-phenyl-3-oxa-1,4-diazabicyclo[4.2.0]oct-2-ene (260 mg, 0.95 mmole), was stirred in acetone (10 ml) together with 1.0N $H_2SO_4$ (30 ml) for 24 hours. After neutralisation with solid $NaHCO_3$ the acetone was removed in vacuo and the aqueous residue extracted with chloroform (3×50 ml). The combined extracts were filtered through anhydrous $Na_2SO_4$ and evaporated in vacuo to give a near colourless oil (205 mg). Purification by mplc on silica gel using a gradient of ethyl acetate/hexane (1:1) increasing to ethyl acetate, gave crystalline solid (145 mg). Recrystallisation from dichloromethane:hexane (1:1) gave 4S-benzoyl-3S-(1R-hydroxyethyl)-trans-azetidin-2-one (121 mg) as colourless plates (m.p. 127°-8° C.); nmr (CDCl$_3$), 200 MHz: delta=1.38(d, 3H); 1.70(broad s, 1H); 2.30 (broad s, 1H); 3.27(sextet, 1H); 4.37(unresolved octet, 1H), 5.10 (d, J=2.7 Hz, 1H); 6.46 (broad s, 1H); 7.53(m, 2H); 7.15 (m, H); 8.15(m, 2H) ppm. The mass spectrum using Past Atom Bombardment had a positive M+H=220 Daltons.

The product of (1) above may be converted to yield a carbapenem or penem by known methods for example as described in EP 126587, EP181831 or GB 2144419, or J. Amer. Chem. Soc. (107) 1438-9 (1985).

EXAMPLE 2

(1'R,6S,7S)-2,2-Dimethyl-7-(1-hydroxyethyl)-8-oxo-5-phenyl-3-oxa-1,4-diazabicyclo[4.2.0]oct-2-ene 5,6-Dihydro-6,6-dimethyl-5-(2R,3R-epoxybutanoyl)-3-phenyl-4H-1,2,5-oxadiazine (570 mg, 2.0 mmole), was stirred in dried, distilled THF (12 ml) under argon at 5° C. A 1M solution of lithium bistrimethylsilylamide in hexane (3.0 ml) was added via a syringe over 3 minutes.

The reaction was stirred to room temperature for 2 hours, and 10% $NaH_2PO_4$ (20 ml), after (50 ml) and ethyl acetate (50 ml) added. The separated aqueous layer was reextracted with ethyl acetate and the combined organic extracts washed with water and then saturated brine. Filtration through anhydrous sodium sulphate and evaporation in vacuo yielded a pale yellow solid (550 mg). Recrystallisation from ether/hexane (1:1) gave (1'R,6S,7S)-2,2-dimethyl-7-(1-hydroxyethyl)-8-oxo-5-phenyl-3-oxa-1,4-diazabicyclo[4.2.0]oct-2-ene (260 mg) as a white solid (mp 176°-8° C. (d)). Analysis: Calculated for $C_{15}H_{18}N_2O_3$(274); C, 65.7; H 6.60; N, 10.2. Found: C, 65.5; H, 6.6; N, 10.0. Nmr (CDCl$_3$; 200 MHz) delta=1.37(d, 3H); 1.44(s, 3H); 1.86(d, 1H); 1.93 (s, 3H); 3.05(q, 1H); 4.25 (sextet, 1H); 4.42 (d, 1H); 7.42(m, 3H); 7.87(m, 2H) ppm.

The mass spectrum showed ions of 274(H$^+$) and 275(m+H) Daltons (EI), and 275 (M+H) Daltons (CI).

EXAMPLE 3

5,6-Dihydro-6,6-dimethyl-5(2R,3R-epoxybutanoyl)-3-phenyl-4H-1,2,5-oxadiazine 2R,3R-Epoxybutanoic acid derived from L-threonine via the corresponding bromohydrin (J. Amer. Chem. Soc 107, 1438-9 (1985); Bull. Chem. Soc. Jap. 52, 949-950 (1979); Nippon Kagaku Zasshi, 87, 459-461 (1960)) (1.53 g 15 mmole nominal) was dissolved in dichloromethane (30 ml) (dried over 4A molecular sieves) and stirred in an ice-bath at 0°-5° C. under argon. 5,6-Dihydro-6,6-dimethyl-3-phenyl-4H-1,2,5-oxadiazine (2.4 g) was added, followed by dicyclohexylcarbodiimide (3.5 g) in dichloromethane (20 ml) dropwise over 15 minutes. After stirring to room temperature for 1 hour, further epoxybutanoic acid (0.6 g) and dicyclohexylcarbodiimide (0.5 g) were added and the reaction stirred overnight at room temperature.

After pouring into saturated $NaHCO_3$ solution, more $CH_2Cl_2$ was added and the organic layer separated and washed with water, 10% $NaH_2PO_4$, water and saturated brine. The residue was then filtered through anhydrous sodium sulphate and evaporated in vacuo to give an oil/solid (5.31 g).

Purification by mplc on silica gel using hexane/ethyl acetate in a gradient of (3.1) to (1.3) gave 5,6-dihydro-6,6-dimethyl-5-(2R,3R-epoxybutanoyl)-3-phenyl-4H-1,2,5-oxadiazine (2.40 g) as a near colourless oil; nmr (CDCl$_3$: 200 MHz) delta=1.28(d, 3H); 1.76(s, 3H); 1.78(s, 3H); 3.36(sextet, 1H); 3.51(d, 1H); 4.24(d, 1H); 4.43(d, 1H); 7.48(m, 3H); 7.79(m, 2H) ppm. The mass spectrum (EI) showed a weak (M+H)$^+$ at 275 Daltons and also by CI, a stronger (M+H)$^+$ion.

EXAMPLE 4

5,6-Dihydro-6,6-dimethyl-3-phenyl-4H-1,2,5-oxadiazine

2-Amino-1-phenylethanone-(Z)-oxime (Ber. 30.1127 (1897)); (7.50 g; 50 mmole) was covered with acetone (100 ml), 4A molecular sieves (5 g) and 2 drops 2N HCl were added.

The mixture was brought to reflux on the steam bath (the reaction was initially exothermic) and stirred under for reflux for 45 minutes. After filtration (hot), evaporation in vacuo to 40-50 ml volume and rapid dilution with 50-60 ml hexane, the product crystallised as white feathery needles. The mixture was cooled for 2 hours and then filtered, washing with a little hexane, and dried in vacuo to give 5,6-dihydro-6,6-dimethyl-3-phenyl-4H-1,2,5-oxadiazine (8.20 g) mp 93°–5° C. Analysis: Calculated for $C_{11}H_{14}N_2O$; C, 69.4; H, 7.4; N, 14.7; Found: C, 69.4; H, 7.5; N, 14.7. Nmr (200 MHz, CDCl$_3$) delta=1.48(s, 6H); 1.96(broad s, 1H); 3.80(s, 2H); 7.38(m, 3H); 7.64(m, 2H). Mass spectrum showed (M+)=190 (EI) and (M+H)+ =191 Daltons (CI).

EXAMPLE 5

5,6-Dihydro-6,6-spirocyclohexyl-3-phenyl-4H-1,2,5-oxadiazine

2-Amino-1-phenylethanone-(Z)-oxime (3.00 g; 20 mmole), cyclohexanone (3.0 g), 4A molecular sieves (3 g) and 2 drops 2N HCl in tetrahydrofuran (25 ml) were stirred under reflux for 45 minutes. Further cyclohexanone (0.5 g) was added and the mixture was stirred under reflux for a further 60 minutes.

The mixture was cooled, a small portion of sodium bicarbonate was added, the mixture was filtered and evaporated under reduced pressure to give a pale yellow solid moist with cyclohexanone. This was taken up in dichloromethane (10 ml) and diluted with 60°–80° petrol (35 ml) to give the title compound as crystalline needles, m.p. 122°–4° C. Analysis: Calculated for $C_{14}H_{18}N_2O$; C, 73.0; H, 7.9; N, 12.2; found; C, 73.2; H, 8.1; N, 12.1. NMR (90 MHz, CDCl$_3$) δ1.65(m, 10H); 1.8(br s, 1H); 3.73(s, 2H); 7.35(m, 3H); 7.60(m, 2H). Mass Spectrum (M+H)=231 (CI) Daltons.

PREPARATION 1

2-Amino-1-phenylethanone-(Z)-oxime (Phenacylamine syn-oxime)

This procedure is an adaption and improvement on the published procedure (Ber. 30.1127 (1897)).

Phenacylamine HCl (17.20 g, 0.10 mole) was stirred in water (80 ml) with hydroxylamine HCl (15.2 g, 0.22 mole) at room temperature. Caustic liquor (10.8N. NaOH, 70° TW: 20 ml) was added dropwise over 5 minutes. After 2 hours at room temperature further caustic liquor (2 ml) was added and the reaction stirred for a further 22 hours.

After 24 hours in total further caustic liquor (10 ml) was added increasing the amount of already precipitated creamy solid. After 4 hours the solid was filtered on a sinter. The damp solid was transferred to a beaker in ca. 60 ml deionised water, stirred for 5 minutes and refiltered with an additional clean water wash (10 ml). The mixture was semi-dried under light vacuum overnight and combined with a further quantity of white solid, filtered off and washed (which had separated overnight from the original mixture). The combined slightly damp solids were suspended in ethanol (150 ml), brought to reflux and as soon as a clear solution obtained, cooled to ca. 50° C. and hexane (100 ml) added. Cooling for 2 hours gave slightly pale yellow plates (11.32 g), mp 137°–9° (d). The mixture, on evaporation in vacuo, trituration of the residue in ether, filtration and recrystallisation of the resulting solid in the same manner gave further product (0.58 g) with the same melting point. Total yield was 11.90 g (80%). An nmr spectrum showed the following resonances in DMSO-d$_6$ (90 HM$_z$): delta=2.80–3.75 (broad s, 2H): 3.76(s, 2H); 3.99–5.5 (broad s, 2H); 7.40(m, 3H); 7.67(m, 2H) ppm.

I claim:

1. A compound of the formula (V):

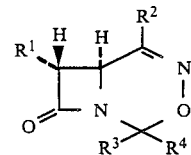

wherein: $R^1$ is $C_{1-4}$alkyl or $C_{1-4}$ alkyl substituted by at least one hydroxy group or protected hydroxy group or fluoro; $R^2$ is hydrogen, $C_{1-4}$ alkyl or phenyl optionally substituted by $C_{1-4}$ alkoxy, $C_{1-4}$ alkyl or halo; and $R^3$ and $R^4$ are independently $C_{1-4}$ alkyl, phenyl optionally substituted by $C_{1-4}$ alkoxy, $C_{1-4}$ alkyl or halo or together with the carbon atom to which they are attached form a $C_{4-7}$ cycloalkyl ring optionally substituted by $C_{1-4}$ alkyl.

2. A compound according to claim 1 wherein $R^1$ is 1-hydroxyethyl.

3. A compound according to claim 1 wherein $R^2$ is phenyl and $R^3$ and $R^4$ are independently methyl.

* * * * *